United States Patent [19]

DeGeeter et al.

[11] 4,316,901
[45] Feb. 23, 1982

[54] ANIMAL FEED AND PROCESS

[75] Inventors: Melvin J. DeGeeter; John M. McCall, both of Kalamazoo, Mich.

[73] Assignee: The Upjohn Company, Kalamazoo, Mich.

[21] Appl. No.: 161,943

[22] Filed: Jun. 23, 1980

[51] Int. Cl.³ .................. A61K 31/505; A61K 31/53; A61K 27/00
[52] U.S. Cl. .................. 424/251; 424/249; 424/248.55
[58] Field of Search .................. 424/251, 248.55, 249

[56] References Cited

U.S. PATENT DOCUMENTS

| | | | |
|---|---|---|---|
| 3,737,534 | 6/1973 | Thommen | 424/251 |
| 3,803,313 | 4/1974 | Collins | 424/251 |
| 3,870,793 | 3/1975 | Collins | 424/251 |
| 4,150,131 | 4/1979 | Muller et al. | 424/251 |
| 4,175,190 | 11/1979 | Muller et al. | 554/323 |

FOREIGN PATENT DOCUMENTS

863608   2/1978   Belgium .............................. 424/251

*Primary Examiner*—Frederick E. Waddell
*Attorney, Agent, or Firm*—John J. Killinger

[57] ABSTRACT

A process for increasing production in meat-producing, egg-laying or milk-producing animals comprising feeding a compound of the formula:

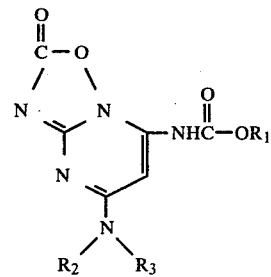

Formula I wherein $R_1$ is a member selected from the group consisting of alkyl of from 1 to 8 carbon atoms, inclusive, including isomeric forms thereof, $R_2$ and $R_3$ are the same or different and are a member selected from the group consisting of hydrogen, provided that both $R_2$ and $R_3$ are not hydrogen; alkyl of from 1 to 8 carbons, inclusive, including isomeric forms thereof, cycloalkyl of from 3 to 8 carbona toms, alkyl substituted cycloalkyl of the formula

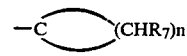

wherein n is an integer of from 2 to 7, inclusive, and $R_7$ is a member selected from the group consisting of hydrogen and alkyl of from 1 to 5 carbon atoms, inclusive, including isomeric forms thereof; alkenyl of from 2 to 8 carbon atoms, inclusive, including isomeric forms thereof, aralkyl wherein Ar is a member selected from the group consisting of phenyl, substituted phenyl wherein 1 or 2 hydrogens are replaced with chlorine, fluorine, bromine, iodine, $R_6$, $-OR_6$, or $-CF_3$ and the substituents can be the same or different, and $R_6$ is alkyl of from 1 to 4 carbon atoms, inclusive, including isomeric forms thereof; and $R_2$ and $R_3$ taken together with $-N<$ is a heterocyclic moiety of from 4 to 8, inclusive, ring atoms and 1 or 2 hetero atoms selected from the group consisting of nitrogen, oxygen, or sulfur, or a substituted heterocyclic moiety wherein 1, 2, or 3 of the carbon atoms of the heterocycle are substituted with $R_1$.

6 Claims, No Drawings

ANIMAL FEED AND PROCESS

DESCRIPTION

BRIEF SUMMARY OF THE INVENTION

Broadly the present invention encompasses a nutritionally adequate animal feed having dispersed therein a compound of the Formula I in sufficient concentration to provide increasing productivity and feed efficiencies in healthy meat-producing, milk-producing or egg-laying animals. The invention also includes the process of administering the composition to meat-producing, milk-producing or egg-laying animals.

BACKGROUND OF THE INVENTION

It has been found in recent years that meat-producing animals will gain more weight and gain it faster when various classes of compounds such as vitamins, minerals, estrogens, antibiotics, and tranquilizers are added to the diet. Although the presently available compounds are useful, new materials are still being sought that would produce weight gains more rapidly, to a greater extent, more efficiently with respect to feed intake at a lower cost and without undesirable side effects.

The active compounds of the present invention of the Formula are known.

DETAILED DESCRIPTION OF THE INVENTION

It is now possible by use of the present invention to obtain unexpected results in the feeding of meat-producing, milk-producing, or egg-laying animals; that is to say, an increased rate of weight gain, an increased amount of weight gain, an increase in milk production, or increased rate of egg laying, as well as increased feed efficiency, can be obtained by the addition of minute quantities of a compound of the Formula to the animals usual nutrient feed or their drinking water.

The active compounds are oxadiazine and are represented by the structure:

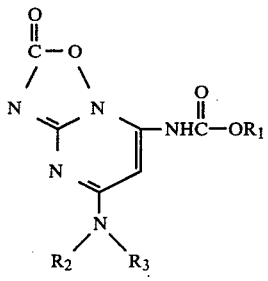

Formula I wherein $R_1$ is a member selected from the group consisting of alkyl of from one to 8 carbon atoms, inclusive, including the isomeric forms thereof, $R_2$ and $R_3$ are the same or different and are a member selected from the group consisting of hydrogen, provided that both $R_2$ and $R_3$ are not hydrogen; alkyl of 1 to 8 carbons, inclusive, including isomeric forms thereof; cycloalkyl of from 3 to 8 carbon atoms, alkyl substituted cycloalkyl of the formula

wherein n is an integer of from 2 to 7, inclusive, and $R_7$ is a member selected from the group consisting of hydrogen and alkyl of from 1 to 5 carbon atoms, inclusive, including isomeric forms thereof; alkenyl of from 2 to 8 carbon atoms, inclusive, including isomeric forms thereof, aralkyl wherein Ar is a member selected from the group consisting of phenyl, substituted phenyl wherein 1 or 2 hydrogens are replaced with chlorine, fluorine, bromine, iodine, $R_6$, —$OR_6$ or —$CF_3$ and the substituents can be the same or different and $R_6$ is alkyl of from 1 to 4 carbon atoms, inclusive, including isomeric forms thereof, and $R_2$ and $R_3$ taken together with —N< is a heterocyclic moiety of from 4 to 8, inclusive, ring atoms and 1 to 2 hetero atoms selected from the group consisting of nitrogen, oxygen, or sulfur, or a substituted heterocyclic moiety wherein 1, 2, or 3 of the carbon atoms of the heterocyclic are substituted with $R_1$.

The compounds of the Formula exist in tautomeric forms. It is to be understood that the compounds of this invention are likely to be mixtures of tautomeric forms, the compositions of which are dependent on such factors as the nature of the substituents and the environment. In some instances, one form or another may predominate.

Compounds of the Formula can be prepared by methods disclosed in Belgian Pat. No. 863,608 issued Mar. 18, 1978 and U.S. Pat. Nos. 4,175,190 and 4,150,131.

The compounds of the Formula I are amines, and exist in the non-protonated or free base form, or in the protonated or acid addition salt form, depending on the pH of the environment. They form stable protonates, i.e., mono- or diacid addition salts, on neutralization with suitable acids, for example, hydrochloric, hydrobromic, sulfuric, phosphoric, nitric, acetic, benzoic, salicyclic, glycolic, succinic, nicotinic, tartaric, maleic, malic, pamoic, methanesulfonic, cyclohexanesulfamic, picric, and lactic acids, and the like.

Examples of alkyl are methyl, ethyl, propyl, butyl, pentyl, hexyl, heptyl, octyl, and isomeric forms thereof. Examples of alkenyl are allyl, 1-methylallyl, 2-methylallyl (methallyl), 2-butenyl (crotyl), 3-butenyl, 1,2-dimethylallyl, 1,1-dimethylallyl, 2-ethylallyl, 1-methyl-2-butenyl, 2-methyl-2-butenyl, 3-methyl-2-butenyl, 3-pentenyl, 2,3-dimethyl-2-butenyl, 1,1,2-trimethylallyl, 1,3-dimethyl-2-butenyl, 1-ethyl-2butenyl, 4-methyl-2-pentenyl, 2-ethyl-2-pentenyl, 4,4-dimethyl-2-pentenyl, 2-heptenyl, 2-octenyl, 5-octenyl, 1,4-dimethyl-4-hexenyl, and the like. Examples of cycloalkyl are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 3-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, and the like. Examples of aralkyl are benzyl, phenethyl, 1-phenylethyl, 2-phenylpropyl, 4-phenylbutyl, 6-pentylhexyl, 5-phenyl-2-methylpentyl, 1-naphthylmethyl, 2-(1-naphthyl)ethyl, 2-(2-naphthyl)ethyl, and the like. Examples of acyl are acetyl, propionyl, butanoyl, pentanoyl, and the like. Examples of alkoxycarbonyl are carbomethoxy, carboethoxy, and the like. Examples of heterocyclic moieties of the present invention are piperidino, pyrrolidinyl, morpholino, 2,4,4-trimethylazetidinyl, 2,3,4-trimethylazetidinyl, 2-methylpyrrolidinyl, 3-butylpyrrolidinyl, 2-isohexylpyrrolidinyl, 2,3-dimethylpyrrolidinyl, 2,2-dimethylpyrrolidinyl, 2,5-diethylpyrrolidinyl, 3-tert-butylpyrrolidinyl, 2,3,5-trimethylpyrrolidinyl, 3,4-dioctylpyrrolidinyl, 2-methylpiperidino, 3-methylpiperidino, 4-methylpiperidino, 3-isopropylpiperidino, 4-tert-butylpiperidino, 2-methyl-5-ethylpiperidino, 3,5-dipentylpiperidino, 2,4,6-trimethylpiperidino, 2,6-dimethylpiperidino, 2,6-dimethyl-4-octylpiperidino, 2,3,5-triethylpiperidino, 2-ethylhexahydroazepinyl, 4-tert-butylhexahydroazepinyl, 3-heptylhexahydroazepinyl, 2,4-dimethylhexahydroazepinyl, 3,3-dimethylhexahydroazepinyl, 2,4,6-tripropylhexahydroazepinyl, 2-methylheptamethylenimino, 5-butylheptamethylenimino, 2,4-diisopropylheptamethylenimino, 3,3-diethylheptamethylenimino, 2,5,8-trimethylheptamethylenimino, 3-methyloctamethylenimino, 2,9-diethyloctamethylenimino, 4-isooctyloctamethylenimino, 2-ethylmorpholino, 2-methyl-5-ethylmorpholino, 3,3-dimethylmorpholino, 2,6-di-tert-butylmorpholino, 4-methylpiperazinyl, 4-isopropylpiperazinyl, 2-methylaziridinyl, 2-ethylaziridinyl, 2-butylaziridinyl, 2,3-dimethylaziridinyl, 2,2-dimethylaziridinyl, 2-methylazetidinyl, 3-methylazetidinyl, 2-octylazetidinyl, 2,2-dimethylazetidinyl, 3,3-diethylazetidinyl, and the like.

Unless otherwise specified, all percentages are given on a weight-to-weight basis. The pound (lb) weights given are avoirdupois units.

Feeding of the compositions of the present invention can commence for birds shortly after hatching and in the case of mammals, during the creep-feeding period of suckling animals when they are starting on solid food and, of course, after weaning. Feeding of the compositions is continued throughout the growing period, lactation period, or egg-laying period.

The total concentration of the compound of the Formula I in the feed composition is determined with regards to the species of animal, age, weight, and average amount of feed consumed daily. Preferably the compounds of the Formula I is employed in the finished feed that will supply the animal with a daily intake of from about 0.02 mg to about 200 mg per head, per day.

The following table illustrates the range of compound of Formula I in milligrams daily dose per head, per day for representative animals.

| Animal | Range Daily Dose/Head, mg | Preferred Daily Dose, mg |
|---|---|---|
| Swine (birth to 8 weeks) | 0.5–20.0 | 10.0 |
| Swine (40 to 200 lbs) | 1.0–140.0 | 50.0 |
| Chickens (growing 0–8 weeks) | 0.02–2.0 | 0.05 |
| Hens (laying) | 0.1–2.0 | 1.0 |
| Turkeys (growing 0–24 weeks) | 0.1–5.0 | 2.0 |
| Beef Cattle (fattening) | 0.5–50.0 | 10.0 |
| Calves (0–12 weeks) | 1.0–40.0 | 10.0 |
| Dairy Cattle (lactation) | 5.0–200.0 | 10.0 |
| Lambs (fattening) | 1.0–20.0 | 10.0 |

The foregoing dosage can generally be accomplished by providing from about 50 mg to about 20,000 mg of a compound of the Formula Ia or Ib per ton of finished feed.

Advantageously a compound of Formula I is supplied in the form of a liquid or solid premix wherein the concentration is 100—2000 times greater than the desired final concentration of the feed. For example, the compound of Formula I can be dissolved or suspended in a fluid vehicle such as corn oil, cottonseed oil, molasses, distillers solubles and the like to prepare a fluid premix. Alternatively, a solid premix can be prepared by mixing a compound of the Formula I with an edible solid diluent such as sucrose, lactose, starch, corn meal, flour, calcium carbonate, soybean meal, and the like.

Example 1

A diet for fattening lambs is prepared from the following types and amounts of ingredients:

| Ground ear corn | 82.05% |
|---|---|
| Alfalfa meal | 10.0% |
| Soybean oil meal 44% | 7.0% |
| Ground limestone | 0.3% |
| Salt | 0.3% |
| Trace mineral mixture[1] | 0.05% |

[1]Contains the following percent of minerals: Mn,12; Co, 0.08; Fe, 5.0; Cu, 0.04; I, 0.24; Zn, 0.7.

The above feed to be mixed, pelleted and offered to fattening lambs free-choice in conjunction with hay.

To 999 parts of the preceding feed is added one part of a premix composition prepared by mixing 7 gm of [2-oxo-5-(1-piperidinyl)-2H-[1,2,4]oxadiazolo[2,3-a]pyrimidin-7-yl]carbamate with sufficient corn meal to make one pound.

The feeding composition so prepared supplies 7.0 mg of ethyl [2-oxo-5-(1-piperidinyl)-2H-[1,2,4]oxadiazolo[2,3-a]pyrimidin-7-yl]carbamate per pound or 15.4 parts per million.

The foregoing composition is usefully fed to lambs for increased rate of weight gain and improved utilization of feed.

Example 2

A chicken feed for broilers is prepared from the following types and amounts of ingredients:

| Yellow corn meal | 67.35% |
|---|---|
| Soybean oil meal | 24.00% |
| Menhaden fish meal | 6.00% |
| Steamed bone meal | 1.00% |
| Ground limestone | 1.00% |
| Iodized salt | .34% |
| 25% Choline chloride | .13% |
| Vitamin $B_{12}$ supplement (6 mg/lb) | .10% |
| Manganese sulfate | .02% |
| Supplemental vitamin mix[1] | .06% |

[1]Consisting of 16.0 gm Vitamin A supplement (10 units/mg); 3.6 gm Vitamin $D_3$ supplement (15,000 units/gm); 7.1 gm riboflavin supplement (1 gm riboflavin per ounce); 500 mg niacin.

To 999 parts of the preceding feed is added 1 part of a premix composition prepared by mixing 0.38 gm of ethyl[2-oxo-5-(1-piperidinyl)-2H-[1,2,4]oxadiazolo[2,3-a]pyrimidin-7-yl]carbamate with sufficient soybean mill feed to make one pound.

The feeding composition so prepared supplies 0.38 mg of ethyl[2-oxo-5-(1-piperidinyl)-2H-[1,2,4]oxadiazolo[2,3-a]pyrimidin-7-yl]-carbamate per pound, or about 0.83 parts per million.

The foregoing composition is usefully fed to chickens for increased rate of weight gain and improved utilization of feed. Similarly the composition can be fed to turkeys, ducks and geese.

Example 3

A fattening feed for 800 pound yearling cattle is prepared from the following types and amounts of ingredients:

| | |
|---|---|
| Ground ear corn | 89.75% |
| Soybean oil meal, 44% | 9.0% |
| Ground limestone | 0.7% |
| Salt | 0.5% |
| Trace mineral mixture[1] | 0.05% |

[1]Contains the following percent of minerals: Mn, 12; Co, 0.08; Fe, 5.0; Cu 0.4; I, 0.24; Zn, 0.7.

To 999 parts of the preceding feed is added one part of a premix composition prepared by mixing 1.5 gm of ethyl[2-oxo-5-(1-piperidinyl)-2H-[1,2,4]oxadiazolo[2,3-a]pyrimidin-7-yl]carbamate with sufficient wheat flour to make one pound.

The feeding composition so prepared supplies 0.5 mg of ethyl[2-oxo-5-(1-piperidinyl)-2H-[1,2,4]oxadiazolo[2,3-a]pyrimidin-7-yl]-carbamate per pound, or about 11.0 parts per million.

Cattle are to receive the foregoing feed ad libitum together with five pounds of hay per head, per day and when so fed have an increased rate of weight gain and improved utilization of feed.

Example 4

A swine diet for growing hogs of 40 to 100 pounds body weight is prepared from the following types and amounts of ingredients:

| | |
|---|---|
| Corn, ground | 78.15% |
| Soybean oil meal, 44% | 17.0% |
| Meat and bone scraps, 50% | 3.0% |
| Oyster shell flour | 0.4% |
| Bone meal | 0.5% |
| Salt | 0.5% |
| Trace mineral mixture[1] | 0.05% |
| Zinc oxide | 0.01% |
| Vitamin A and D supplement[2] | 0.25% |
| B Vitamin supplement[3] | 0.05% |
| Vitamin $B_{12}$ supplement[4] | 0.09% |

[1]Contains the following percent of minerals; Mn, 12; Co, 0.08; Fe, 5.0; Cu, 0.4; I, 0.24; Zn, 0.7.
[2]Contains 300 USP units $D_3$/Gm and 1500 I.U.A./Gm.
[3]Contains per lb.: Riboflavin, 2000 mg.; calcium pantothenate, 4000 mg.; niacin, 9000 mg.; and choline chloride 10,000 mg.
[4]Contains 6 mg Vitamin $B_{12}$ per pound.

To 999 parts of the preceding feed is added one part of a premix composition prepared by mixing 10 gm of ethyl[2-oxo-5-(1-piperidinyl)-2H-[1,2,4]oxadiazolo[2,3-a]pyrimidin-7-yl]carbamate with sufficient ground limestone to make one pound.

The feeding composition so prepared supplies 10 mg of ethyl[2-oxo-5-(1-piperidinyl)-2H-[1,2,4]oxadiazolo[2,3-a]pyrimidin-7-yl]-carbamate per pound, or about 22 parts per million.

The foregoing composition is usefully fed to hogs for increased rate of weight gain and improved utilization of feed.

Example 5

A regimen of ethyl[2-oxo-5-(1-piperidinyl)-2H-[1,2,4]oxadiazolo-[2,3-a]pyrimidin-7-yl]carbamate in water is prepared simply by adding the compound to the drinking water as specified below. The animlas are allowed to ingest the water on an ad libitum basis.

| | | |
|---|---|---|
| Swine | birth to 8 weeks | 2.5 |
| Swine | 40-200 lb. | 7.0 |
| Chickens | 0-8 weeks | 0.3 |
| Hens | | 5.0 |
| Turkeys | 0-24 weeks | 3.2 |
| Beef cattle | | 0.2 |
| Calves | 0-12 weeks | 1.0 |
| Dairy cattle | | 0.9 |
| Lambs | | 5.0 |

Example 6

Following the procedure of the preceding Examples 1 to 4, inclusive, animal feeds are similarly prepared substituting equimolar amounts of:

ethyl[5-[3,6-dihydro-1(2H)-pyridyl]-2-oxo-2H-[1,2,4]-oxadiazolo-[2,3-a]pyrimidin-7-yl]carbamate;

butyl[5-[3,6-dihydro-1(2H)-pyridyl]-2-oxo-2H-[1,2,4]oxadiazolo-[2,3-a]-pyrimidin-7-yl]carbamate;

ethyl[5-dialkylamino-2-oxo-2H-[1,2,4]-oxadiazolo[2,3-a]-pyrimidin-7-yl]carbamate.

An added advantage was observed in the feeding of sheep. The sheep produced an increased amount of wool. This increase in wool production was attributable to the increase in body size (and weight).

We claim:

1. A process for obtaining increased production in meat-producing, egg-laying, or milk-producing animals comprising feeding to said animals an effective amount of a compound of the formula:

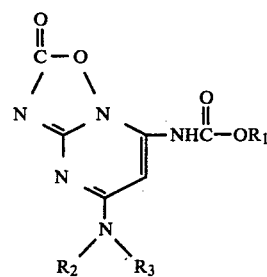

Formula I wherein $R_1$ is a member selected from the group consisting of alkyl of from 1 to 8 carbon atoms, inclusive, including isomeric forms thereof, $R_2$ and $R_3$ are the same or different and are a member selected from the group consisting of hydrogen, provided that both $R_2$ and $R_3$ are not hydrogen; alkyl of from 1 to 8 carbons, inclusive, including isomeric forms thereof, cycloalkyl of from 3 to 8 carbon atoms, alkyl substituted cycloalkyl of the formula

wherein n is an integer of from 2 to 7, inclusive, and $R_7$ is a member selected from the group consiting of hydrogen and alkyl of from 1 to 5 carbon atoms, inclusive, including isomeric forms thereof; alkenyl of from 2 to 8 carbon atoms, inclusive, including isomeric forms thereof, aralkyl wherein Ar is a member selected from the group consisting of phenyl, substituted phenyl wherein 1 or 2 hydrogens are replaced with chlorine, fluorine, bromine, iodine, $R_6$, —$OR_6$, or —$CF_3$ and the substituents can be the same or different, and $R_6$ is alkyl of from 1 to 4 carbon atoms, inclusive, including isomeric forms therof; and $R_2$ and $R_3$ taken together with —N< is a heterocyclic moiety of from 4 to 8, inclusive, ring atoms and 1 or 2 hetero atoms selected from the group consisting of nitrogen, oxygen, or a substituted heterocyclic moiety wherein 1, 2, or 3 of the carbon atoms of the heterocycle are substituted with $R_1$.

2. The process of claim 1 where the member selected is fed in combination of from 0.001 mg to 10 mg per kilogram body weight of the animal per day.

3. The process of claim 1 where the member selected is ethyl-[2-oxo-5-(1-piperidinyl)-2H-[1,2,4]oxadiazolo[2,3-a]pyrimidin-7-yl]carbamate.

4. The process of claim 1 wherein the animal is a meat-producing animal.

5. The process of claim 1 wherein the animal is an egg-laying animal.

6. The process of claim 1 wherein the animal is a milk-producing animal.

* * * * *